United States Patent [19]

Ohfume et al.

[11] Patent Number: 4,959,493
[45] Date of Patent: Sep. 25, 1990

[54] CARBOXYCYCLOPROPYLGLYCINE AND PROCESS FOR PRODUCING THE SAME

[75] Inventors: Yasufumi Ohfume; Keiko Shimamoto, both of Osaka; Haruhiko Shinozaki, Omiya, all of Japan

[73] Assignee: Suntory Limited, Osaka, Japan

[21] Appl. No.: 184,920

[22] Filed: Apr. 22, 1988

[30] Foreign Application Priority Data

Jun. 30, 1987 [JP] Japan .................. 62-163179

[51] Int. Cl.$^5$ ........................... C07C 101/20
[52] U.S. Cl. .................................. 562/506
[58] Field of Search ....................... 562/506

[56] References Cited

PUBLICATIONS

Tetrahedron Letters, vol. 29, No. 10, pp. 1181–1184, Mar. 1, 1988.

Primary Examiner—Michael L. Shippen
Attorney, Agent, or Firm—Cushman, Darby & Cushman

[57] ABSTRACT

A novel compound (2S,3R,4S)-carboxycyclopropylglycine represented by the formula (1):

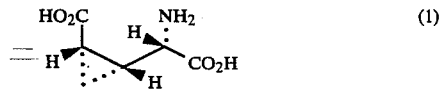

(1)

has proved to be the most potent agonist for the N-methyl-D-aspartate (NMDA) receptor which is one of the glutamate receptor sub-types in the mammalian central nervous system. This compound provides useful tools to open a road to the development of glutamic acid receptor antagonists that may have thereapeutic value in epilepsy, neuronal disorders such as Huntington's chorea and Parkinsonism, as well as various acute and chronic neurodegerative disorders.

Also disclosed is a process for producing this compound, as well as a process for individually synthesizing four carboxycyclopropylglycine steroisomers including those of the following formulas (1a, 1b, 1c):

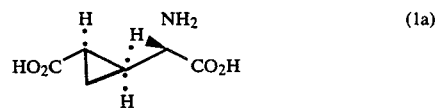

(1a)

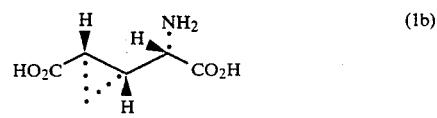

(1b)

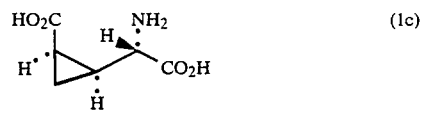

(1c)

and the formula (1).

1 Claim, No Drawings

CARBOXYCYCLOPROPYLGLYCINE AND PROCESS FOR PRODUCING THE SAME

BACKGROUND OF THE INVENTION:

The present invention relates to (2S,3R,4S)-carboxycyclopropylglycine represented by the formula (1):

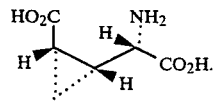

(1)

It also relates to a process for producing this compound, as well as a process for individually synthesizing four carboxycyclopropylglycine stereoisomers including those of the following formulas (1a, 1b, 1c):

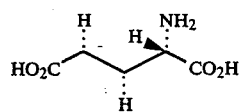

(1a)

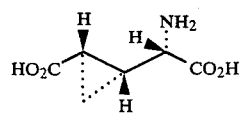

(1b)

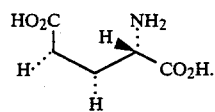

(1c)

L-glutamic acid has been considered to be one of the most probable excitatory neurotransmitters in the mammalian central nervous system. The (2S,3R,4S)-carboxycyclopropylglycine (1) of the present invention has proved to be one of the most potent excitatory amino acid-agonist by activating specifically to N-methyl-D-aspartate (NMDA) type receptor which is one of the glutamate receptor sub-types in the mammalian central nervous system. This compound provides useful tools to open a road to the development of glutamic acid receptor antagonists that may have therapeutic value in epilepsy, neuronal disorders such as Huntington's charea and Parkinsonism, as well as various acute and chronic neuro-degenerative disorders.

The four stereoisomers (1, 1a, 1b, 1c) provided by the present invention are anticipated to offer important contributions for elucidation of the mechanism of L-glutamic acid receptor interaction on the basis of the correlation between the conformations of L-glutamic acid (including their analogs) and the activities thereof.

L-glutamic acid has drawn the attention of researchers as an excitatory neurotransmitter in the mammalian central nervous system and unraveling the mechanism of its agonist-receptor interaction is one of the most important subjects currently being dealt with by life science.

Since Watkins et al. succeeded in discovering L-glutamic acid agonists using L-glutamic acid related amino acids in 1961 (D. R. Curtis, J. W. Phillips, J. C. Watkins; British J. Pharmacology, 16, 262–283, 1961), a number of substances analogous to L-glutamic acid have been found date that exhibit neuronal excitatory activities.

As a result of the recent active studies conducted to unravel the function of the L-glutamic acid receptor using L-glutamic acid agonists, these receptors have been classified into the following three subtypes (J. C. Watkins, R. H. Evans; Annu. Rev. Pharmacol., 21, 165–204, 198I): N-methyl-D-aspartate (NMDA), kainate (KA), and quisqualate (QA). It has been suggested that receptors cells of the individual subtypes are distributed in certain associated sites in the central nervous system while being directly related to their corresponding neuro-physiological functions [(a) D. T. Monaghan, V. R. Holets, D. W. Toy, C. W. Cotman; Nature, 306, 176–179, 1983; (b) D. T. Monaghan, D. Yao, C. W. Cotman; Brain Res., 324, 160–164, 1984; (c) H. J. Oversman, D. T. Monaghan, C. W. Cotman, J. C. Watkins; Eur. J. Pharmac., 131. 161–162, 1986]. If the relationship between L-glutamic acid agonists and their receptors were to be unravelled at the molecular level, a great contribution would be rendered to the current efforts being made to search for more patent specific antagonists, as well as to develop glutamic acid receptor blocking agents that may have clinical therapeutic value in epilepsy, movement disorders, neuronal disorders such as Hutchinson's disease and Parkinsonism, as well as various acute and chronic neurodegenerative disorders (B. Meldrum; ISI Atlas of Science, 228–232, 1987).

Such being the circumstances surrounding the efforts so far made in studying the mechanism of L-glutamic acid reception, nobody has ever succeeded in unravelling the structural relationship between L-glutamic acid agonists and L-glutamic acid which could lead to the development of effective antagonists. While it has been shown that L-glutamic acid receptors can be classified into the three subtypes, NMDA, KA and QA, the only explanation so far proposed to structurally relate these subtypes to L-glutamic acid is that the conformation of the latter would contribute to efforts to distinguish these subtypes (J. C. Watkins, H. T. Olverman; Trend in Neuroscience, 10, 265–272, 1987). It is therefore very important to characterize the correlation between the conformation of L-glutamic acid and its activity before the mechanism of L-glutamic acid receptor interaction can be unravelled at the molecular level.

L. Fowden et al. isolated trans- and cis-carboxycyclopropyl-L-glycine (1a, 1c) from *Aesculus parviflora* and *Blighia sapida* and found that they caused undesired effects such as hypoglycemia and vomiting (L. Fowden et al.; Phytochemistry, 8, 437, 1969). Ohfune et al. reported the synthesis of a racemate of transcarboxycyclopropylglycine (1a, 1b) from dl-β-acetoxyalkylglycine (Ohfune et al.; Tetrahedron Lett., 26, 83, 1985). However, the trans- and cis-carboxycyclopropyl-L-glycine (1a, 1c) are present in plants in very small amounts and the two other stereoisomers (1b, 1d) are absent. The method reported by Ohfune et al. is merely capable of yielding a racemate of 1a, 1b for the following two principal reasons: the intermediate [3,3]-sigmatropic rearrangement product, is labile and has no stereoselectivity for cyclopropanation; the diastereomers are difficult to separate. No non-native (2S,3R,4S)-carboxycyclopropylglycine (1) has been known in the art, nor any process for producing the same. Neither has any process been reported for synthesizing the four possible stereoisomers as the optically active forms of carboxycyclopropylglycine.

SUMMARY OF THE INVENTION:

With a view to unraveling the relationship between the conformation of L-glutamic acid and its activity in adjunct with the investigation of the agonist-receptor interaction, the present inventors synthesized analogs with the fixed confirmation of L-glutamic acid, namely, four types of carboxycyclopropyI-L-glycine (1, 1a, 1b, 1c), and found that 3R,4S)-carboxycyclopropylglycine (1), a novel stereo-isomer among these analogs, exhibited a potent excitatory activity specific to the NDMA type receptor. The present inventors also succeeded in developing a method capable of stereospecific synthesis of this novel isomer. The present invention has been accomplished on the basis of these results.

The novel compound of the present invention, namely, (2S,3R,4S)-carboxycyclopropylglycine (1), can be produced by the following process. First, the synthesis of the four stereoisomers (1, 1a, 1b, 1c) is described. A (2S)-2-aminobutenol derivative of the general formula (7):

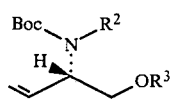
(7)

(where Boc is a t-butoxycarbonyl group; $R^2$ is a hydrogen atom; $R^3$ is a hydrogen atom, a t-butyldimethylsilyI group, or a group capable of forming a dimethylmethylene group when combined with $R^2$) is reacted with ethyl diazoacetate in the presence of a palladium salt, preferably palladium (II) acetate, to form a mixture of the four stereoisomers of a opropylglycinol derivative of the general formula (8):

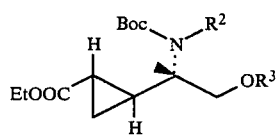
(8)

(where Boc, $R^2$ and $R^3$ are the same as defined above). The resulting mixture is reacted with an acid or (n-Bu)₄NF to form an alcohol, which is subjected to column chromatography on silica gel, thereby separating carboxycyclopropane derivatives of the formulas (9b) and (9c):

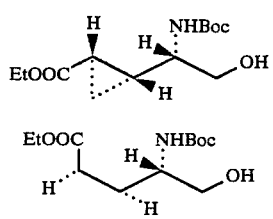
(9b)

(9c)

The two other isomers are inseparable and their mixture is heated together with DL-camphor-10-sulfonic acid and subjected to another run of column chromatography on silica gel, thereby separating a caraboxycyclopropane derivative of the formula (9a) and lactone (5) of isomer (9d), respectively:

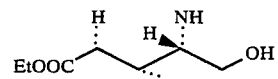
(9a)

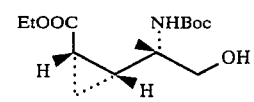
(9b)

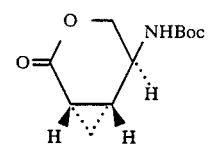
(5)

The so obtained compounds (9a), (9b) and (9c) are processed by standard procedures consisting of Jones oxidation, alkali hydrolysis and a final treatment with trifluoroacetic acid to obtain the desired carboxycyclopropylglycine isomers (1a), (1b) and (1c).

The lactone of formula (5) is treated with an alkali to have the lactone ring opened, and subsequently treated with diazomethane into a methyl ester form. The methyl ester is processed by standard procedures consisting of Jones oxidation, alkali hydrolysis and a final treatment with trifluoroacetic acid to obtain the carboxycyclopropylglycine formula (1).

The (2S,3R,4S)-carboxycyclopropylglycine of formula (1) can be synthesized stereospecifically by the following method. First, a butenol derivative of the formula (2):

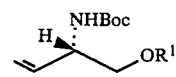
(2)

(where $R^1$ is a t-butyldimethylsilyl group; and Boc is a t-butoxycarbonyl group) is oxidized with ozone in an inert solvent such as methanol at 0° C. or below, and the resulting ozonide is reactively decomposed by standard procedures to obtain an aldehyde derivative. In the next step, methyl bis-2,2,2-trifluoroethylphosphorylacetate is reacted with sodium hydride in a solvent such as tetrahydrofuran in an inert gas atmosphere to form a ylide solution. To this ylide solution, 18-crown-6 followed by the previously prepared aldehyde derivative is added to form a pentenoic acid ester of the formula (3):

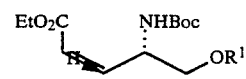
(3)

(where $R^1$ and Boc are the same as defined above).

The so obtained pentenoic acid ester (3) is reacted with an acid, preferably, DL-camphor-10-sulfonic acid, in an inert solvent such as methanol, whereupon the ester readily cyclizes into a lactone of the formula (4):

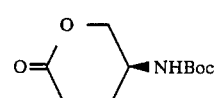
(4)

(where Boc is the same as defined above).

The lactone (4) is dissolved in a solvent, preferably ether, and reacted with a diazomethane solution, whereupon a bicyclolactone of the formula (5):

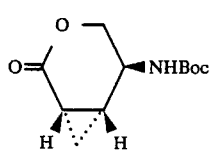
(5)

(where Boc is the same as defined above) is obtained with a stereoselectively of at least 85%.

The bicyclolactone (5) is subsequently treated by the standard method already described to obtain the (2S,3R,4S)-cyclopropylglycine (1) of the present invention in high yield.

If it is presumed that the L-glutamate receptor accepts specific conformations of L-glutamic acid, the conformations to be received are divided into two types, an extended conformation and a folded conformation. Of the four compounds synthesized by the present invention, compounds (1a) and (1b) mimic the former conformation and compounds (1) and (1c) mimic the latter conformation. The difference in configuration at β-position of these carboxycyclopropylglycine is believed to be a key factor in explaining the steric element in the interaction with the receptors. Physiological activity tests with an isolated new-born rat spinal cord showed that compound (1a) exhibited the activity of an agonist of the kainate type. Compound (1) was 100 times as active as L-glutamic acid and was found to be the most potent substance ever known as an agonist of the NMDA type.

The following examples are provided for the purpose of further illustrating the present invention but are in way to be taken as limiting.

EXAMPLE 1

Step 1

(2S)-N-t-butoxycarbonyl-ethoxycarbonylcyclopropylglycinol t-butyldimethylsilyl ether:

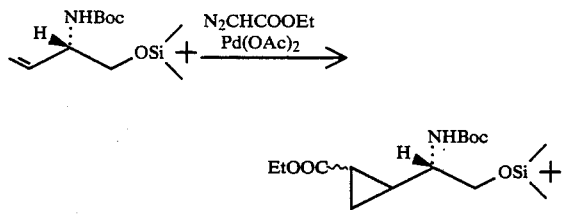

163 mg (0.72 mmol) of palladium (II) acetate was dissolved in 4.20 g (14.5 mmol) of (2S)-N-t-butoxycarbonyl-2-amino-3-butenol t-butyldimethylsilyl ether. To the resulting solution, an ether solution (300 ml) of 17.1 g (150 mmol) of ethyl diazoacetate was added over 4 hours. The insoluble matter was filtered out and the filtrate was concentrated under vacuum to obtain an oil. The oil was purified by column chromatography on silica gel (20% ether/hexane), and the end compounds were obtained as a mixture of four stereoisomers. The yield was 1.96 g (36.1%) and the mixture was a colorless oil.

Step 2

N-t-butoxycarbonyl-ethoxycyclopropylglycinol:

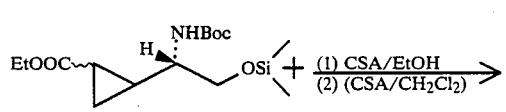

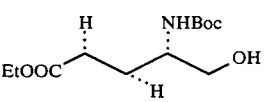
9a(2S,3S,4S)

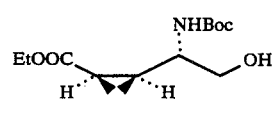
9c(2S,3S,4R)

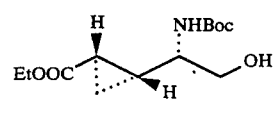
9b(2S,3R,4R)

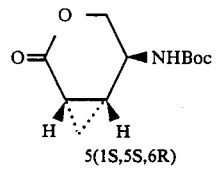
5(1S,5S,6R)

1.90 g (4.9 mmol) of the silyl ether form was dissolved in 30 ml of ethanol. To the solution, 5 mg of DL-camphor-10-sulfonic acid was added and the mixture was stirred at room temperature for 16 hours. The solvent was distilled off under vacuum and the residue was subjected to medium-pressure silica gel column chromatography (50% ether/hexane); 418 mg of (2S,3R,4R) isomer (9b), 124 mg of (2S,3S,4R) isomer (9c), 156 mg of mixture of (2S,3S,4S) isomer (9a) and (2S,3R,4S) isomer, and 342 mg of a mixture thereof were obtained [total yield, 1.04 g (77.7%)]. 414 mg of a mixture of (2S,3S,4S) isomer (9a) and (2S,3R,4S) isomer was dissolved in methylene chloride and 3 mg of DL-camphor-10-sulfonic acid was added to the solution, followed by stirring for 18 hours. The reaction solution was washed with a saturated aqueous solution of sodium hydrogen carbonate. The organic layer was dried over magnesium sulfate, filtered and concentrated under vacuum. The residue was subjected to medium-pressure silica gel column chromatography (75% ether/hexane) to give 230 mg of (2S,3S,4S) isomer (9a) and 80 mg of lactone form (5) of (2S,3R,4S) isomer (9d).

(2S,3S,4S) isomer (9a)

Nature: colorless oil $^1$H-NMR (360 MHz, CDCl$_3$) δ(ppm): 0.94(1H,m), 1.20(1H,m), 1.28(3H,t,J=7.5Hz), 1.45(9H,s), 1.55(1H,m), 1.77(1H,m), 2.65(1H,s), 3.17(1H,m), 3.60-3.80(2H,m), 4.13(2H,dq,J=7.5, 13Hz), 4.96(IH,d,J=9Hz)

IR spectrum (cm$^{-1}$): 3372, 2984, 1712

$[\alpha]_D^{25}$ +72.9° (C=0.55, CHCl$_3$)

(2S,3R,4R)isomer (9b)

Nature: colorless needle (recrystallized from ether-hexane)

m.p.: 88.0°–89.0° C.

$^1$H-NMR (360 MHz, CDCl$_3$) δ(ppm): 1.03(1H,m), 1.17(1H,m), 1.25(3H,t,J=7Hz), 1.44(9H,s), 1.57(2H,m), 2.74(IH,s), 3.22(1H,m), 3.60–3.77(2H,m), 4.11 (2H,dq,J=7.14Hz), 4.96(1H,d,J=8Hz), IR spectrum (film, cm$^{-1}$) 3460, 3028, 1712

$[α]_D^{25}$ −47.2° (C=0.55, CHCl$_3$)

(2S,3S,4R) isomer (9c)

Nature: colorless needle (recrystallized from ether-hexane)

94.0°–95.0° C.

$^1$H-NMR (360 MHz, CDCl$_3$) δ(ppm): 1.15(2H,m), 1.27(3H,t,J=7Hz), 1.53(1H,m), 1.77(1H,m), 3.02(1H,bs), 3.61(1H,m), 3.65–3.90(2H,m), 4.15(2H,dq,J=7.14Hz), 4.95(1H,s)

IR spectrum (film, cm$^{-1}$): 3392, 2984, 1716

$[α]_D^{25}$ −56.0° (C=0.48, CHCl$_3$)

Step 3

(A) (2S,3R,4R)-carboxycyclopropylglycine (1b):

200 mg (0.73 mmol) of (2S)-N-t-butoxycarbonylethoxycyclopropylglycinol (9b) was dissolved in 10 ml of acetone and the solution was stirred for 3 hours under cooling with ice in the presence of a Jones reagent. Following stirring for an additional 1.5 hours at room temperature, isopropanol was added under cooling with ice to decompose the excess reagent. After adding an aqueous solution of sodium hydrogen carbonate, the mixture was washed with ether and the unreacted starting material was removed. The aqueous layer was adjusted to pH 2 with citric acid and extracted with ethyl acetate. The organic layer was washed with water, dried over magnesium sulfate and freed of the solvent by distillation under vacuum. The residue was dissolved in 3 ml of tetrahydrofuran and stirred for 19 hours with ice after the addition of 1.5 ml of an aqueous solution of 0.5 N sodium hydroxide. The reaction solution was adjusted to pH 2 with 1N HCl and saturated by the addition of crystalline sodium chloride, then with ethyl acetate. The organic layer was dried over magnesium sulfate and thereafter the solvent was distilled off under vacuum to obtain 152 mg (80.0%) of N-t-butoxycarbonyl-(carboxycyclopropyl)glycine as an oil. This was dissolved in 2 ml of methylene chloride and the solution was stirred for 30 minutes under cooling with ice after the addition of 2 ml of trifluoroacetic acid. The residue obtained by concentration under vacuum was loaded on a column of an ion-exchange resin (Dowex 50W×4). After washing with water, the column was eluted with 1N aqueous ammonia to obtain an ammonium salt of the end compound. This was dissolved in water and adjusted to pH 3 with 1N HCl. The resulting crystal was collected by filtration and recrystallized from water to obtain 75.2 mg of the titled compound as a white crystal.

m.p. 255°–258° C.

$^1$H-NMR (360 MHz, D$_2$O) δ(ppm): 1.15(1H,m), 1.32(1H,m), 1.76(1H,m), 1.95(1H,m), 3.40(1H,d,J=9.0 Hz)

$[α]_D^{25}$ −15.1° (C=0.49, H$_2$O)

(B) (2S,3S,4S)-carboxycyclopropylglycine (1a):

By repeating the procedure of step 3(A), 24.1 mg of the titled compound (colorless crystal) was obtained from 230 mg of compound (9a).

m.p.: 243°–247° C. (decomposed with foaming)

$^1$H-NMR (360 MHz,D$_2$O) δ(ppm): 1.25(1H,ddd,J=9.1, 5.7, 5.1 Hz), 1.34(1H,ddd,J=9.1, 9.1, 5.1 Hz), 1.71(1H,m), 1.78(1H,ddd,J=9.1 5.1, 4.0 Hz), 3.23(1H,d,J=9.8Hz)

$[α]_D^{21}$ +102.0° (C=0.50, H$_2$O) {$[α]_D^{20}$ +107° (C2, H$_2$O) in the literature}

(C) (2S,3S,4R)-carboxycyclopropylglycine (1c):

By repeating the procedure of step (A), 16.1 mg of the titled compound (colorless crystal) was obtained from 100 mg of compound (9c).

m.p.: 178°–180° C.

$^1$H-NMR (360 MHz, D$_2$O) δ(ppm): 1.18(1H,ddd,J=6, 6, 5Hz), 1.46(1H,ddd,J=8.5, 8.5, 5Hz), 1.68(1H,m), 1.92(1H,ddd,J=8.5, 6.6Hz), 3.94(1H,d,J=10 Hz)

$[α]_D^{22}$ +20.7° (C=0.46, H$_2$O) {$[α]_D^{20}$ +25° (C=1, H$_2$O) in the literature}

(D) (2S,3R,4S)-carboxycyclopropylglycine (1):

Eighty milligrams (0.35 mmol) of the lactone form (5) prepared in Step 2 was dissolved in 1 ml of tetrahydrofuran and the solution was stirred for 14 hours under cooling with ice after addition of an aqueous solution of 0.5N potassium hydroxide. The mixture was adjusted to pH 1 with 1N HCl under cooling with ice and extracted with ethyl acetate. The organic layer was washed with water, dried and freed of the solvent by vacuum distillation. The residue was dissolved in methanol and a solution of diazomethane in ether was added to make a methyl ester form. This was subsequently treated as in Step 3(A) to obtain 14.4 mg of the titled compound (colorless crystal).

m.p.: 178°–180° C.

$^1$H-NMR (360 MHz, D$_2$) δ (ppm): 1.06(1H,ddd,J=8.5, 7, 5Hz), 1.22(1H,ddd,J=8.5, 8.5, 5Hz), 1.61(1H,ddd,J=9, 8.5, 7.7Hz), 1.94(1H,ddd,J=8.5, 8.5, 7Hz), 3.89(IH,d,J=gHz)

$[α]_D^{25}$ +97.1° (C=0.52, H$_2$O)

EXAMPLE 2

Step 1

Methyl (4S)-4-(N-t-butoxycarbonyl)amino-5-t-butyldimethyl-silyloxy-3(Z)-pentenoate (3):

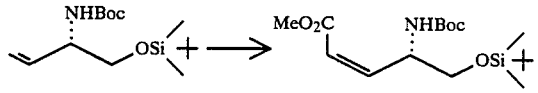

Six hundred milligrams (1.95 mmol) of (2S)-2(N-t-butoxycarbonyl)amino-3-butenol silyl ether was dissolved in 10 ml of methanol and the solution was oxidized with ozone at −78° C. To this solution was added 5 ml of dimethylsulfide at −78° C. to decompose the resulting ozonide which upon standing at −78° C. for 2 hours and at room temperature for 3 hours gave an aldehyde form with a cleaved double bond. The solvent was distilled off under vacuum and the oily residue was chromatography using 10 g of silica gel, to give 564 mg of an aldehyde form (yield, 95%).

Without being further purified, the compound was subjected to the following reaction. A solution of 881 mg (2.77 mmol) of methyl bis-2,2,2-trifluoroethylphosphorylacetate in tetrahydrofuran (5 ml) was added dropwise to a suspension of 111 mg (2.77 mmol) of sodium hydride in tetrahydrofuran (10 ml) at 0° C. in a nitrogen stream, and the mixture was stirred for 30 minutes. To the reaction solution which was cooled to −78° C., a solution of 3.65 g (13.85 mmol) of 18-crown-6 in THF (10 ml) and a solution of 564 mg (1.85 mmol) of aldehyde in THF (5 ml) were successively added dropwise and the mixture was stirred for 2 hours at the same temperature.

To the reaction mixture, 10 ml of a saturated aqueous solution of ammonium chloride was added at −78° C. and the mixture was slowly warmed to room temperature. Following the addition of 50 ml of water, an extraction with ether was repeated three times. The combined organic layers were dried over 5 g of anhydrous magnesium sulfate and the solvent was distilled off under vacuum. The residue was subjected to silica gel column chromatography to give the titled compound in an amount of 495 mg (yield, 74%).

Nature: oil

IR (neat) (cm$^{-1}$) 3464, 3388, 2960, 2936, 1724, 1652
NMR (CDCl$_3$) δ: 0.08(3H,s), 0.09(3H,s), 0.92(9H,s), 1.48(9H,s), 3.76(3H,s), 3.80(3H,m), 4.87(1H,d,J=11.5Hz), 5.20(1H,dd,J=8.0, 11.5Hz)

Step 2

(4S)-4-(N-t-butoxycarbonyl)amino-2-penten-5-olide (4):

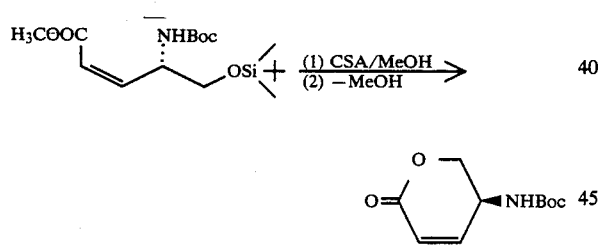

330 mg (0.918 mmol) of methyl (4S)-4-(N-t-butoxycarbonyl)amino-5-t-butyldimethylsilyloxy-3(Z)-pentenoate was dissolved in 5 ml of methanol and the solution was stirred for 16 hours after the addition of 10 mg of DL-camphor-10-sulfonic acid. The reaction mixture was quenched by an addition of an aqueous solution of sodium hydrogen carbonate and extracted with ethyl acetate. The organic layer was washed with water, dried over magnesium sulfate and concentrated under vacuum. The residue was dissolved in 5 ml of chloroform and concentrated to obtain a lactone form as a colorless crystal in an amount of 180 mg (92.3%).

Nature: colorless crystal
m.p.: 12.5°–122.5° C.
$^1$H-NMR (100 MHz, CDCl$_3$) δ(ppm): 1.47(9H,s), 4.2–4.6(3H,m), 4.80(1H,b), 6.70(1H,d,J=10Hz), 6.86(1H,dd,J=5, 10Hz)
IR (cm$^{-1}$): 3340, 2988, 1724, 1686
$[α]_D^{23}$ +62.5° (C=1.01, CHCl$_3$)

Step 3

(1S,5S,6R)-5-(N-t-butoxycarbonyl)amino-3-oxabicyclo[4.I.0]hepta-2-one (5):

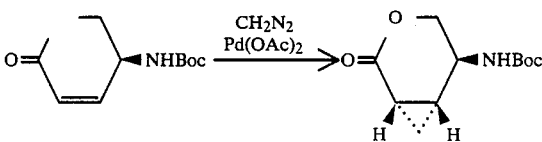

116 mg (0.516 mmol) of palladium (II) acetate was dissolved in a solution of 100 mg (0.469 mmol) of unsaturated actone in 10 ml of ether. To the solution, a solution of diazomethane in ether was added until the starting material disappeared on TLC. After filtration of the insoluble materials, the filtrate was concentrated under vacuum and the residue was purified by column chromatography on silica gel (90% ether/hexane), so as to obtain 33 mg (31.1%) of the end compound as a 6:1 mixture of the threo form (1S,5S,6R) and the erythro form (1R,5S,6S).

Test

In accordance with the method described in Evans, R. H. and Watkins, J. C., European J. Pharmac., 50 123-129, 1978, the minimum effective concentrations (MEC) of L-glutamic acid and compounds (1), (1a), (1b) and (1c) of the present invention for causing depolarizations of motoneurons in the isolated spinal cord of a neonatal rat under perfusion with an artificial physiological solution (spiral fluid) were measured as extracellular records in the neutral root. The test results are shown in Table 1.

TABLE 1

| Compound | MEC (molar concentration) | Specific activity |
| --- | --- | --- |
| L-Glu*$^1$ | 1 × 10$^{-4}$ | 1 |
| (1) | 1 × 10$^{-6}$*2 | 100 |
| (1a) | 0.5 × 10$^{-4}$*3 | 5 |
| (1b) | (−)*4 | (−) |
| (1c) | 5 × 10$^{-4}$ | 0.5 |

*$^1$L-glutamic acid
*$^2$Activity disappeared in the presence of Mg$^{++}$ ions
*$^3$Unaffected in the presence of Mg$^{++}$ ions
*$^4$Ineffective The glutamic acid receptors in the mammalian central nervous system are classified into three subtypes, NMDA, KA and QA. Compound (1) of the present invention whose activity disappeared in the presence of Mg$^{++}$ ions is believed to act on the NMDA type receptor As Table 1 shows, this compound is 100 times as potent as L-glutamic acid and 5 times more potent than NMDA which has previously been considered the most potent agonist with an activity of 2×10$^{-5}$ in molar concentration. Because of this high activity, compound (1) has great potential for use as a tool in neurotransmission testing of the central nervous system.

What is claimed is:

1. (2S,3R,4S)-carboxycyclopropylglycine of the formula (1):

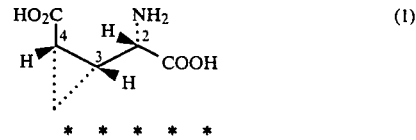

* * * * *